(12) United States Patent
Samson

(10) Patent No.: US 8,846,332 B2
(45) Date of Patent: Sep. 30, 2014

(54) MICROPLATE COMPRISING A CONTINUOUS PERIPHERAL CHANNEL

(75) Inventor: Arnaud Samson, Dremil-Lafage (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 0 days.

(21) Appl. No.: 13/395,737

(22) PCT Filed: Sep. 10, 2010

(86) PCT No.: PCT/FR2010/000615
§ 371 (c)(1),
(2), (4) Date: Mar. 13, 2012

(87) PCT Pub. No.: WO2011/030018
PCT Pub. Date: Mar. 17, 2011

(65) Prior Publication Data
US 2012/0178120 A1    Jul. 12, 2012

(30) Foreign Application Priority Data
Sep. 14, 2009 (FR) ..................... 09 56292

(51) Int. Cl.
*C12Q 1/02* (2006.01)
*C12M 1/34* (2006.01)
*C12M 1/32* (2006.01)
*B01L 3/00* (2006.01)

(52) U.S. Cl.
CPC ........ *C12M 23/12* (2013.01); *B01L 2300/0829* (2013.01); *B01L 3/5085* (2013.01)
USPC .......................................... 435/29; 435/288.3

(58) Field of Classification Search
USPC ................................. 435/29, 288.3
See application file for complete search history.

(56) References Cited

U.S. PATENT DOCUMENTS

| | | | |
|---|---|---|---|
| 5,587,321 A | 12/1996 | Smith et al. | |
| 5,908,776 A | 6/1999 | Burbaum et al. | |
| 7,208,125 B1 | 4/2007 | Dong | |
| 7,820,433 B2 * | 10/2010 | Larsen | 435/305.3 |

FOREIGN PATENT DOCUMENTS

| | | |
|---|---|---|
| WO | WO 2006/005811 | 1/2006 |
| WO | WO 2008/111035 | 9/2008 |

OTHER PUBLICATIONS

French Search Preliminary Report for FR0956292 OF Jun. 1, 2010.
International Search Report for PCT/FR2010/000615 of Oct. 17, 2011.

* cited by examiner

*Primary Examiner* — Karen Cochrane Carlson
*Assistant Examiner* — Natalie Moss
(74) *Attorney, Agent, or Firm* — Hueschen and Sage

(57) ABSTRACT

The present invention relates to a microplate, or microtitration plate, having an invagination consisting of a continuous peripheral channel making it possible to add thereto, in a single introduction step, a liquid acting as an "evaporation curtain". The invention is also directed to a device comprising such a microplate, to a manufacturing method and to use of such a microplate.

7 Claims, 4 Drawing Sheets

MICROPLATE COMPRISING A CONTINUOUS PERIPHERAL CHANNEL

The present invention relates to the field of microtitration devices. More especially, the invention relates to a microplate, or microtitration plate, having an invagination consisting of a continuous peripheral channel making it possible to add thereto, in a single introduction step, a liquid acting as an "evaporation curtain".

It is now recognised by various users that the microplates used in laboratories do not provide complete satisfaction insofar as they may cause errors in the analysis of samples. Such errors may be due, especially, to a problem related to the arrangement of the plate. One major problem lies in the fact that within a covered microplate there is an evaporation gradient between the peripheral wells and the central wells. This evaporation gradient observed in the wells of the microplate is the effect of a thermal and/or hydrological gradient between the external environment and the interior of the covered plate, which may be the result of a long period of incubation of the plate and which may then falsify the results of the analyses carried out. In addition, it is to be noted that the temperatures at which biological or biochemical analyses are carried out can be very close to the vaporisation temperatures of some constituents of the samples. This therefore gives rise to vaporisation, that is to say the passage from the liquid state to the gaseous state, of some of the solvents containing the samples or even of the samples themselves. The wells that are adversely affected by this evaporation gradient are chiefly the peripheral wells, because these wells are more readily exposed to high temperatures and to hygrometric variations than the wells in the centre of the plate. Their walls do in fact reach the temperatures of the conservation medium of the samples contained in those microplates more rapidly and they are located closer to the ventilation zone between the outer edge of the plate and the cover, which results in the partial and non-homogeneous evaporation of some constituents. This evaporation phenomenon observed in the peripheral wells, a phenomenon also known by the term "edge effect", may falsify the analyses and the reading of results.

The patent specification U.S. Pat. No. 5,587,321 proposes solving problems of evaporation and condensation by providing a liquid-receiving chamber, said liquid being the first to undergo evaporation owing to its location at the outside of the plate. The liquid-receiving chamber is made up of a large number of chambers surrounding the matrix of wells and extending between the wells and under the matrix. However, this model remains very complex, especially owing to the large number of chambers which surround the matrix of wells and which do not allow constancy of evaporation of the liquid contained in said chambers. Moreover, the complexity of the shape of the chambers surrounding the matrix, including extending under and between the wells, involves costly manufacture in several parts.

Other tests have been carried out in an attempt to optimise microplates, especially adding additional wells around the matrix of wells of the plate. However, the prior art does not propose solutions that are simple to put into practice and that, above all, are completely effective in combating those edge effects.

The present invention proposes solving the problems of edge effects in microtitration plates by adding an invagination around the matrix of wells. This invagination is provided in the form of a continuous peripheral channel which contains a liquid acting as an "evaporation martyr" and which thereby permits the homogeneous conservation and reactivity of the chemical, biochemical or biological materials under the effect of thermal or hydrological variations between the environment and the inside of a microplate.

The microplates may therefore tolerate variations in temperature or hygrometric contrasts without the contents of the wells being degraded, thanks to the compensation that evaporation of the liquid from the continuous peripheral channel allows. Gaseous exchanges between the inside and outside of the microplate are likewise preserved whilst maintaining temperature and humidity in the microplate.

The liquid contained in the peripheral channel accordingly has the function of protecting the peripheral wells by being the first to undergo thermal variations and evaporate off. Evaporation of the liquid from the channel accordingly creates a buffer zone of hydration and thermal compensation of gaseous exchanges between the inside and outside of the covered plate, greatly limiting evaporation and degradation of the samples in the wells. The temperatures of the external environment are first applied to the outside of the microplate. The liquid in the channel will accordingly be the first to evaporate off when the microplate is utilised under the conditions of an experiment.

The present invention accordingly relates to a microplate comprising a base having a matrix of wells and an invagination which is arranged to receive a liquid acting as an evaporation martyr, said microplate being characterised in that said invagination consists of a continuous peripheral channel.

One advantage of the invention is that the microplate described corresponds to the technical specifications for the microplate format defined by the SBS ("Society for Biomolecular Sciences") and ANSI ("American National Standards Institute").

The microplate according to the invention especially comprises a base around a matrix of wells. The base is composed of walls serving as a support for the microplate. It comprises an inner wall, referred to as the "inner wall of the base" and also as the "inner wall of the microplate", and an outer wall, similarly referred to as the "outer wall of the base" or "outer wall of the microplate", given that the inner and outer walls of the microplate correspond to those of the base.

The microplates also have a jutting-out portion in the walls of the microplate. Said jutting-out portion is provided from the inside towards the outside, thereby forming a shoulder on the outer wall of the microplate. The cover placed on the microplate is accordingly held in place by virtue of this shoulder formed by the portion jutting out from the inside towards the outside.

In standard manner, the microplate also comprises a matrix of wells. This matrix may be made up of a variable number of wells arranged to receive that same number of samples for analysis. The number of wells may accordingly vary but the microplate always has the same well alignment arrangement.

The outer wall of the matrix of wells is considered to correspond to the outer wall of the row of peripheral wells.

The arrangement of standard microplates used for carrying out biological or biochemical analysis is well known to the person skilled in the art and will therefore not be described in further detail.

The term "invagination" is defined as a fold of concave shape within the microplate, consisting of a continuous peripheral channel arranged to receive a liquid acting as an "evaporation martyr".

A "liquid acting as an evaporation martyr" is understood to mean a liquid which, when subjected to certain influences, can evaporate off as a "substitute for" the samples present in the peripheral wells of the microplate, as explained hereinbefore.

By way of non-limiting example of a "liquid acting as an evaporation martyr" there may be mentioned water or any type of aqueous solution, including physiological solutions or buffer solutions, serums and culture media, as well as cryo-preservation solutions. In equivalent manner, and by extension, there may be mentioned as a liquid acting as an evaporation martyr any solution which is liquid and which may gel after introduction, which liberates the same kind of vapours as the samples contained in the wells. The typical example is the solvent corresponding to the solvent in which the samples or reagents contained in the wells of said plate are dissolved.

Hereinbelow, unless otherwise indicated, the expressions "invagination" and "continuous peripheral channel" may be used interchangeably.

Likewise, the liquid contained in the continuous peripheral channel may equally be referred to as "liquid acting as evaporation martyr", "liquid acting as evaporation curtain", "liquid in the channel", "liquid in the invagination", "peripheral liquid" or "evaporation liquid".

The continuity of the channel is one of the main characteristics of the present invention. It ensures complete uniformity in terms of temperature and evaporation of the liquid at any point in the channel, the liquid being distributed within one and the same channel around the microplate. The continuity of said channel therefore allows uniformity of the thermal conditions of the liquid. This then results in evaporation of the liquid from the channel, thereby protecting the peripheral wells of the matrix.

In accordance with a first embodiment of the invention, the continuous peripheral channel may share its walls, or edges, with the matrix of wells and also the base. The inner wall of the channel then corresponds to the outer wall of the matrix of wells, and the outer wall of the channel then corresponds to the inner wall of the base.

In accordance with another embodiment of the invention, the continuous peripheral channel may be provided with walls of its own. The channel's "edges of its own" or "walls of its own" are understood to mean walls which said channel does not share with any other element forming the device of the invention.

In other words, the invention relates to a microplate comprising a base having a matrix of wells and an invagination arranged to receive a liquid acting as an evaporation martyr, said microplate being characterised in that said invagination consists of a continuous peripheral channel and has walls of its own.

The outer wall of the channel is therefore juxtaposed to the outer wall of the base, and the inner wall of the channel is juxtaposed to the outer wall of the matrix of wells. The channel's having walls of its own allows said channel to be directly and uniformly subjected to the temperature conditions to which the microplate is subjected.

The inner surface of the microplate in contact with the support on which it is held is not uniformly flat. As explained hereinbefore, the base is composed of walls having a portion jutting out towards the outside of the microplate. The wells of the microplate do not extend as far as said jutting-out portion, thereby forming an empty space underneath the bottom of the wells. This space allows the circulation of ambient air underneath the wells of the matrix. The air circulating underneath the wells and the channel allows the temperatures in experiments to be applied directly underneath the device comprising the peripheral liquid and the samples in the wells. The peripheral channel's having its own walls accordingly allows the liquid in said channel to be subjected to the temperatures more rapidly and therefore to evaporate off more rapidly.

These individual walls also represent an advantage for manufacture of the microplate, as it is preferable for the channel to be isolated from the peripheral wells in order to avoid mechanical stresses during removal from the mould and cooling in the course of manufacture of the device.

In accordance with a preferred embodiment of the invention, the microplate is characterised in that the depth P of said invagination is less than or equal to the depth p of the wells of the matrix.

In order that the liquid contained in the channel is indeed the first liquid that may evaporate off under the effect of the temperatures to which the microplate is subjected, the depth of the channel cannot exceed that of the matrix of wells. It is indeed necessary for the surface of the evaporation liquid to be higher than that of the samples in the wells. It will accordingly be possible for the evaporation liquid to be the first to evaporate off on contact with the environmental conditions of the air circulating underneath the cover.

The liquid in the channel evaporates off under the effect of the temperatures to which the microplate is subjected. This evaporation underneath the cover of the microplate makes it possible, in addition to maintaining the contents of the wells of the matrix unaffected, to stabilise the thermal conditions underneath the cover and above the wells of the matrix.

In accordance with another embodiment, the microplate according to the invention is characterised in that the depth P of said invagination is less than or equal to the height H of that portion of the outer wall of the plate which extends from the top of the plate to the portion jutting out from the inner wall of the base.

This embodiment of the invention has an advantage for storage of the empty microplates, the microplates being stacked one on top of another in industry. The empty space underneath the wells of the matrix accordingly allows the microplates to be stacked using a minimum storage space. The channel should therefore not extend beyond the portion jutting out from the inner edge of the microplate in order to allow stacking of the microplates in a reduced storage volume.

In accordance with a preferred embodiment, the microplate according to the invention is characterised in that the thickness of the bottom of said invagination is the same as the thickness of the bottom of the wells of the matrix.

In order that the thermal conditions are applied in identical manner to the channel and to the wells of the matrix, it is necessary for the bottoms of said channel and of said wells to be similarly composed in terms of thickness.

This also allows savings of plastic and weight for transportation and packaging.

The shape of the continuous peripheral channel is an important characteristic of the invention, as it is responsible for the good evaporation of the liquid that it contains in order to protect the samples within the wells of the matrix from the effects of temperature and hygrometric effects to which the microplate is subjected.

In accordance with a preferred embodiment of the invention, the invagination forming the channel has at least one non-rectilinear wall whose shape matches the circular edge of the row of peripheral wells of the matrix.

Preferably, at least one wall of this channel is non-rectilinear and forms the inner wall, that is to say that which is in the proximity of the outer row of wells. However, for whatever technical reason, it may be the other wall, namely that in the proximity of the outer walls of the microplate.

That particular shape of at least one wall of the continuous peripheral channel has the consequence of extending said channel. The evaporation liquid therefore extends over a longer perimeter around the matrix of wells. In addition to matching the circular shape of the wells of the matrix, the non-rectilinear wall of the channel is located at a constant distance from said wells. The proximity of the channel to the peripheral wells plays a part in evaporation of the liquid from solely the channel and not from the sample in the peripheral wells, which are then protected by said channel. The non-rectilinear shape of the wall of the channel matching the circular edge of the peripheral wells of the matrix has the consequence of maximising the length of the continuous peripheral channel and therefore the volume of the evaporation liquid.

The serpentine shape of the non-rectilinear wall of the channel also plays a part in the stability of the evaporation liquid. Movement of the microplate can in fact bring about movements in the liquid, especially in the continuous channel. Those movements are due to the fact that the peripheral liquid has greater mobility owing to the longitudinal continuity of the channel than the samples in the wells of the microplate. The non-rectilinear shape of at least one wall of the channel can therefore break up the shock waves in the liquid in the channel, limiting the movements of said liquid.

In accordance with another, also preferred, embodiment, the microplate according to the invention is characterised in that said continuous peripheral channel has both walls non-rectilinear, the shape thereof matching the circular edge of the row of peripheral wells of the matrix.

The same advantages as observed in the presence of a single non-rectilinear wall of the channel are also found in the presence of two non-rectilinear walls. The surface of the channel is extended even further and the shock waves due to the mobility of the liquid in the channel are even more controlled and limited by the presence of those two non-rectilinear walls.

According to one particular embodiment of the invention, there may be provided within the peripheral channel, along a perpendicular axis, walls that form a semi-baffle. Such walls must not cross from one side of the peripheral channel to the other in order that the latter maintains its continuous form to ensure it can be readily filled in a single operation. Such baffles will have the effect of breaking up the shock waves in the liquid and of increasing the overall surface tension. The use of a semi-baffle can replace the serpentine shape of the channel or can be provided in addition thereto.

Another advantage of the invention, directly linked to the continuity of the peripheral channel, lies in the fact that the channel-forming invagination has at least one bulge acting as a filling point for said channel.

It is mentioned here that the term "bulge" may be replaced by any synonymous term in the present description, especially by the term "widening".

The continuity of the channel, the main characteristic of the invention, has the advantage that the "evaporation martyr" liquid can be applied to the channel in a single introduction. As the width of the channel does not necessarily allow easy filling, there is added to the channel a bulge of relatively reduced size allowing said filling of the evaporation liquid into the channel.

In preferential manner, said bulge is located in a corner of the microplate. This location accordingly makes it possible to maintain the continuity of the channel all around the wells at the periphery of the microplate. The location of the bulge in the corner of the microplate accordingly makes it possible to reduce the differences in distance that there may be with the wells close to the bulge compared to that of wells next to the channel.

In accordance with a preferred embodiment, the width of the continuous peripheral channel is between 2 millimeters and 2.5 millimeters, inclusive, next to the diameter of the wells and between 5 and 6 millimeters, inclusive, next to the junction between the wells.

This width was calculated so as to be most suitable for existing microplate devices and machines and, amongst other things, allows standard covers to be used. However, it is entirely clear that this width can be changed by the person skilled in the art as a function of developments in the different apparatus.

In practice, the cross-section of the continuous peripheral channel can have various shapes such as, for example, the shape of a cone, an inverted rectangular trapezoid or a rectangle. Generally, there is preferred a slightly trapezoidal shape in order to allow a sufficient draft angle for moulding and so that the liquid spreads all around the channel during filling without trapping bubbles or causing an overflow before the liquid has filled the entire channel. It should not be too conical either, so that the width of liquid in the channel does not diminish too rapidly with lowering of the level of the liquid within it. The protective effect would then diminish too greatly over time, at the very moment when the hydrating effect is most necessary.

Preferably, the microplate according to the invention has a space at the outer periphery of the microplate, said space being sufficiently wide to allow alphanumeric marking of said device.

In view of the number of wells in some microplates, the alphanumeric marking of said wells facilitates use of the microplates by the skilled person. Marking can be carried out on the edge of the microplate on the base. It allows recognition by means of a letter or number in the horizontal and vertical directions. It is therefore important to include that space allowing alphanumeric marking of the wells in the microplate according to the invention.

In standard manner, the microplate according to the invention can be composed of 6, 12, 24, 48, 96, 384 or 1536 wells.

There currently exists a great variety of microplates for carrying out chemical, biological or biochemical analyses, syntheses, reactions, storage or also cell culture. Accordingly, the arrangement of device presented in this patent application is applicable to any type of standard microplate used in analytical, chemical, biological or biochemical laboratories.

In accordance with another aspect, the invention relates to a device comprising a microplate as described hereinbefore and a standard cover arranged so as to cover fully, but not hermetically, the matrix of wells and the evaporation channel of said microplate.

The cover is especially used for the purpose of protecting the samples present in the wells of the microplates. Said cover is a standard cover used in numerous microplate arrangements. It allows maintenance and equilibration of the gaseous exchanges in the microplate above the wells of the matrix and the channel, whilst allowing slight ventilation from the environment of the microplate. Such ventilation is in fact necessary to maintain the viability and/or functionality of certain materials contained in the wells. To this end, the present invention used conjointly with a standard cover allows such ventilation without resulting in evaporation of the contents of the peripheral wells, by virtue of the benefits brought by the channel.

The cover is simply set down on the microplate on the shoulder formed by the portion jutting out from the inside of the base. Said jutting-out portion of the base on the outside of the microplate accordingly allows the cover to be fitted onto the microplate.

In accordance with another aspect, the invention relates to a device comprising a microplate as described hereinbefore and a specific cover arranged to cover fully and hermetically the matrix of wells and the evaporation channel of said microplate. This device then makes it possible to equilibrate the gaseous exchanges above the wells of the matrix and the channel in definitive manner for the purpose of long-term storage of the samples contained in the wells.

In accordance with yet another aspect, the invention is directed towards a method of manufacturing the device mentioned hereinbefore, characterised in that it comprises a first step, of manufacture of the microplate according to the invention, and a second step, of manufacture of the cover.

Manufacture of the microplate in only two steps has a non-negligible industrial advantage for the simplicity of manufacture of the device of the invention. The first step accordingly consists of manufacture of the microplate itself, composed of the base, the continuous peripheral channel and the matrix of wells. It is accordingly made in one single part, characterising its simplicity of manufacture. The second step of manufacture relates to manufacture of the cover of the microplate, a step which presents no difficulty of manufacture given that the cover used for the microplate of the invention is a standard cover.

Finally, according to a last aspect, the invention also encompasses use of a microplate and/or device obtained by carrying out the method of the invention, in the culture and/or primo-culture of eukaryotic and/or prokaryotic cells, tissue and/or proto-organ cultures, and also storage, reactions and analyses of materials, and chemical, biochemical and/or biological reagents.

More especially, and in advantageous manner, the invention is directed towards the above-mentioned use, characterised in that said channel-forming invagination is filled with a liquid in a single introduction.

Filling of the continuous peripheral channel in a single introduction step is possible by virtue of the continuity of the channel. This use accordingly has a certain practicality for the skilled person, who does not need to carry out a plurality of filling operations around the matrix of wells.

The invention will be described in greater detail in the Examples hereinbelow, referring to the following Figures,

Example 1

Figure 1:
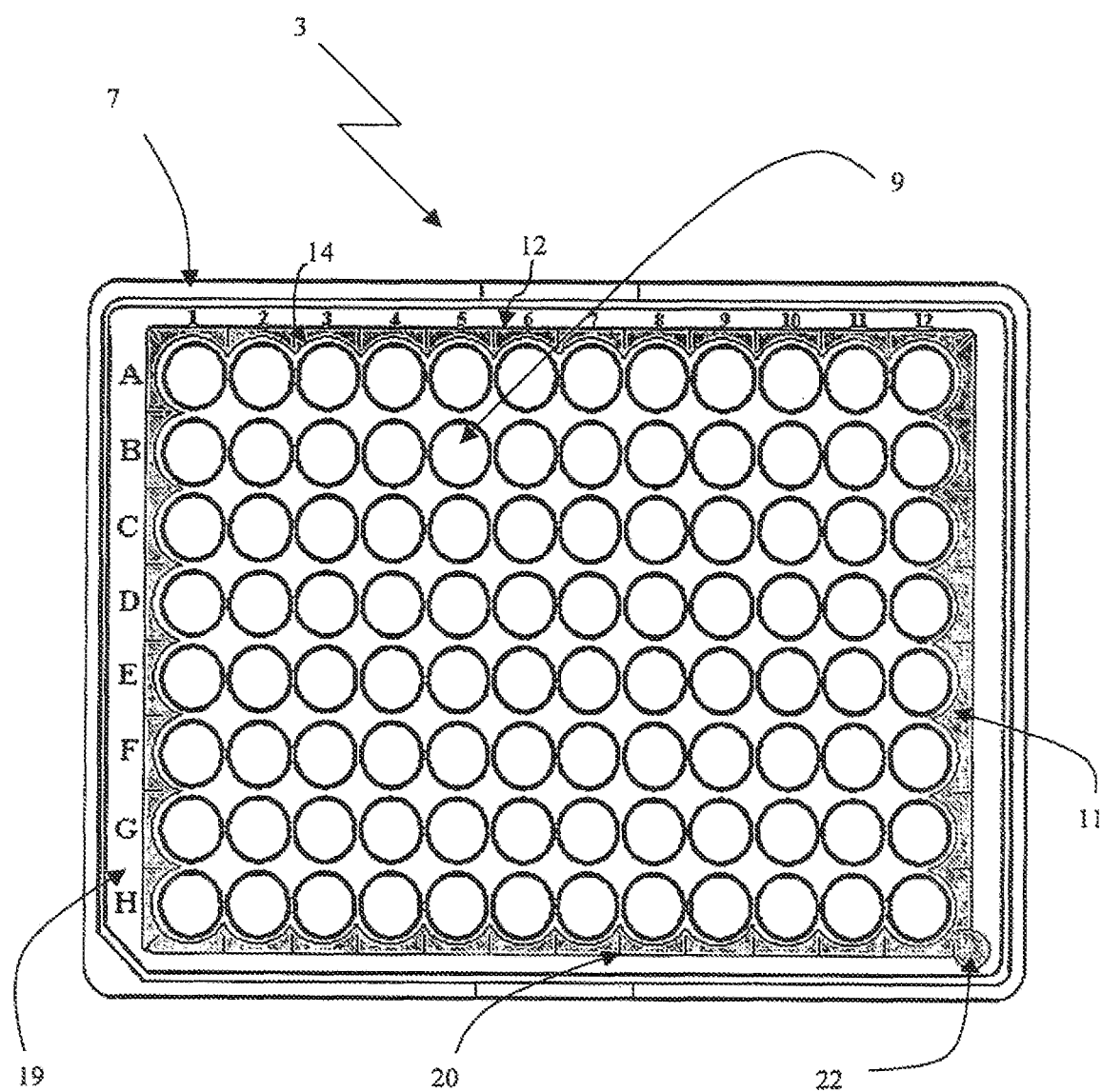
FIG. 1: Top view of a 96-well microplate according to the invention. The device is composed of a microplate (3) and a cover (5) (not shown). The microplate (3) comprises a base (7) surrounding a matrix of wells (9). The microplate (3) also comprises an invagination (11) arranged to receive a liquid acting as an evaporation martyr. The invagination (11) of the microplate (3) consists of a continuous channel around the periphery of the matrix of wells (9). The invagination (11) has walls of its own, an outer wall (12) and an inner wall (14). The invagination (11) has at least one widening or bulge (22) acting as a filling point for the invagination (11). The widening or bulge (22) is located in a corner of the microplate (3). The invagination (11) has semi-baffles (20) located in the channel at the junction between two wells of the matrix (9). The microplate (3) has a space (19) on the outside of the base (7) allowing alphanumeric marking of the device.
Figure 2:
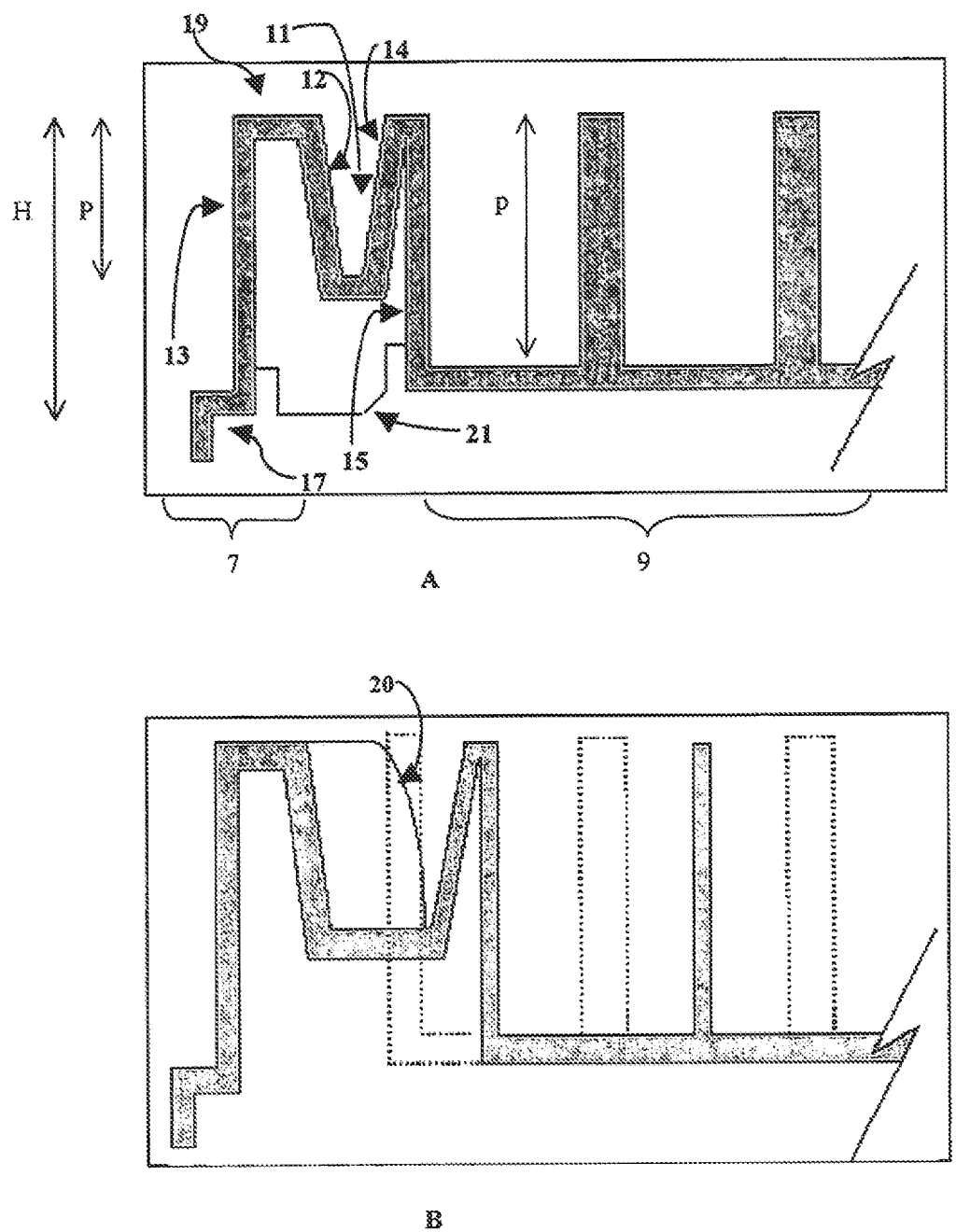
FIG. 2: Cross-sectional view of a first embodiment, at the diameter of the wells (A) and at the junction between the wells (B). The invagination (11) has walls of its own, an outer wall (12) and an inner wall (14) and is located between the outer wall (13) of the base (7) and the outer wall (15) of the matrix of wells (9). The depth P of the continuous peripheral invagination (11) is less than or equal to the depth p of the wells of the matrix (9). The depth P of the peripheral invagination (11) does not extend beyond the height H of the portion (17) jutting out from the inner wall of the base (7). The invagination (11) has at least one non-rectilinear wall (14). The invagination (11) may also have two non-rectilinear walls (12) and (14). The microplate (3) may have reinforcing baffles (21) between the outer wall (13) of the microplate (3) and the outer wall (15) of the matrix of wells (9). The invagination (11) has semi-baffles (20) located in the channel at the junction between two wells of the matrix (9). The microplate (3) has a space (19) on the outside of the base (7) allowing alphanumeric marking of the device.
Figure 3:
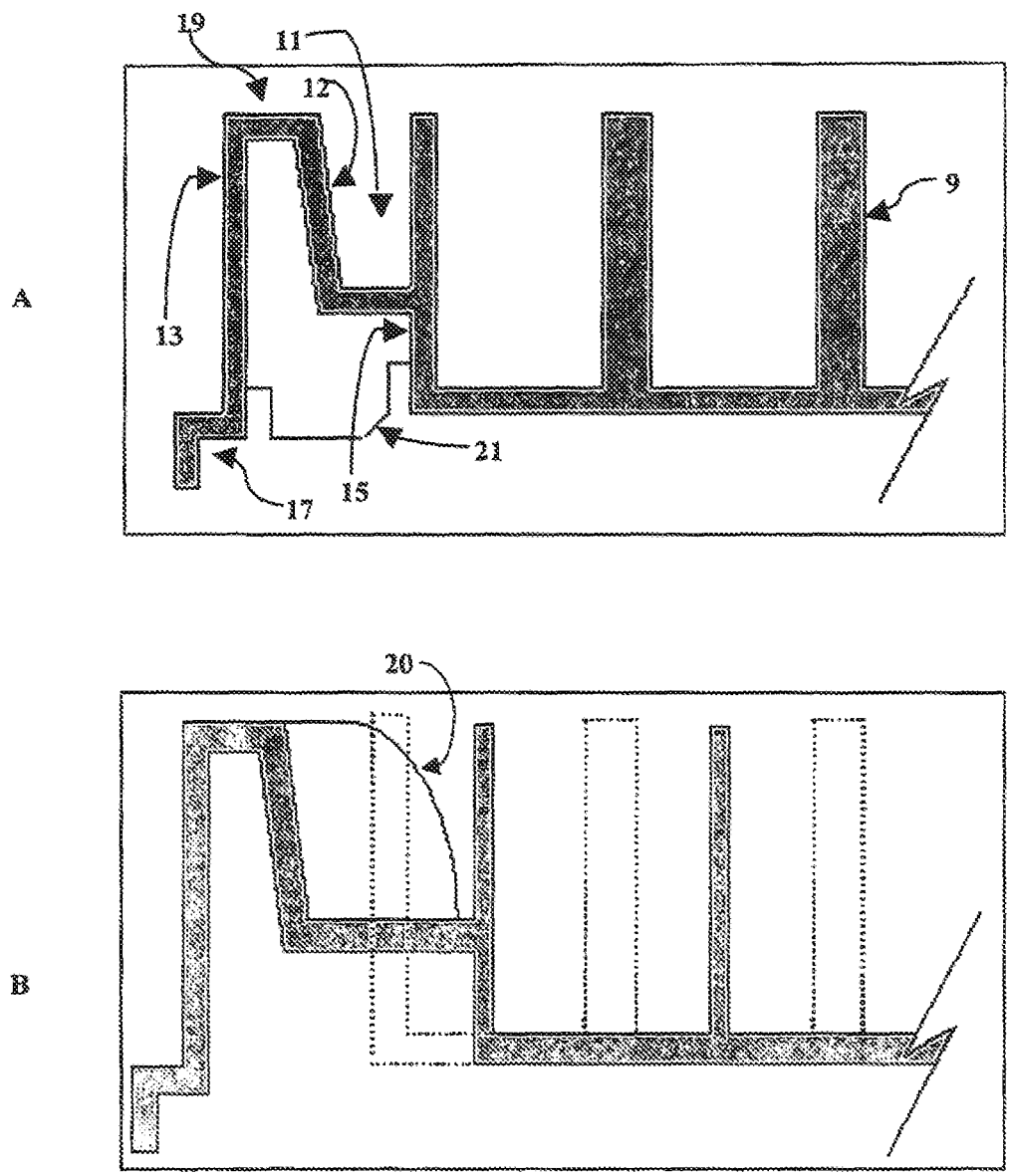
FIG. 3: Cross-sectional view of a second embodiment, at the diameter of the wells (A) and at the junction between the wells (B). The outer wall (15) of the matrix of wells (9) constitutes the inner wall of the invagination (11). The invagination (11) has at least one non-rectilinear wall (12). The microplate may have reinforcing baffles (21) between the outer wall (13) of the microplate and the outer wall (15) of the matrix of wells (9). The microplate has a portion (17) jutting out from the inner wall (13) of the base and a space (19) on the outside of the base allowing alphanumeric, marking of the device.
Figure 4:
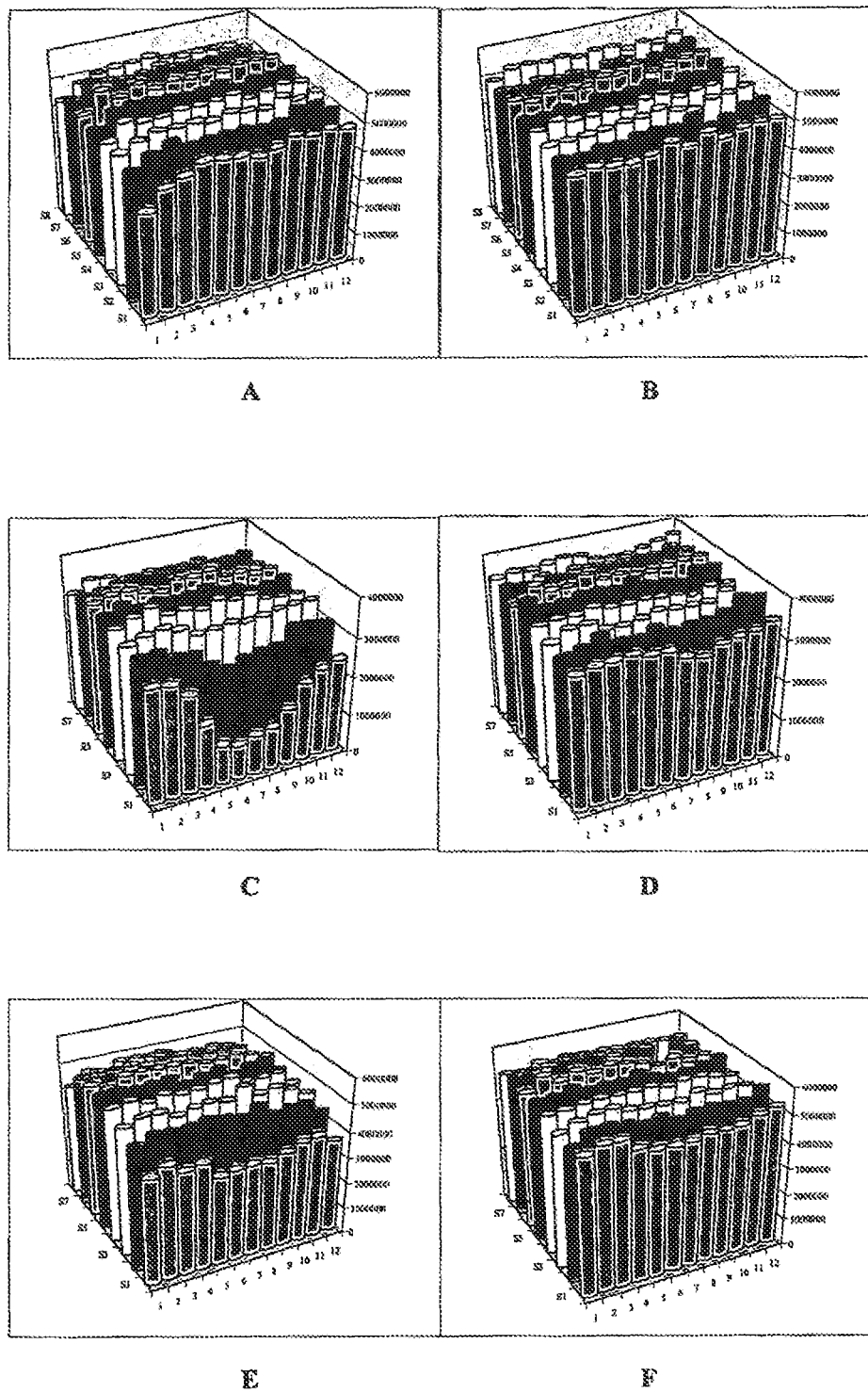
FIGS. 4 (A to F): diagrams illustrating the measurement of cell viability after 3 or 4 days' incubation in commercially available 96-well microplates compared to microplates according to the invention.

Referring to FIGS. 1 to 3, the device is composed of a microplate 3 and a cover 5 (not shown). The microplate 3 comprises a base 7 surrounding a matrix of wells 9. The microplate 3 also comprises an invagination 11 arranged to receive a liquid acting as an "evaporation martyr". As clearly emerges from FIG. 1, said invagination 11 of the microplate 3 consists of a continuous peripheral channel. The continuous peripheral channel 11 is located between the outer wall 13 of the base 7 and the outer wall 15 of the matrix of wells 9. According to a preferred arrangement of the invention shown in FIG. 2, the channel 11 has walls of its own, that is to say an outer wall 12 and an inner wall 14. The depth P of the continuous peripheral column 11 is less than or equal to the depth p of the wells of the matrix. The depth P of the continuous peripheral channel 11 does not extend beyond the height H of the portion 17 jutting out from the inner wall 13 of the base 7. The continuous peripheral channel 11 has at least one non-rectilinear wall 14 whose shape matches the circular edge on each side of the row of peripheral wells of the matrix 9. The continuous peripheral channel 11 may also have two non-rectilinear walls 12 and 14, whose shape matches the circular edge on each side of the row of peripheral wells of the matrix 9 (embodiment not shown).

In accordance with another preferred arrangement of the invention shown in FIG. 3, the outer wall 15 of the matrix of wells 9 constitutes the inner wall (14 in FIG. 2) of the channel 11.

The channel 11 has, within it, semi-baffles 20 located in the channel at the junction between two wells in the preferred arrangements of FIGS. 1 to 3.

The microplate described according to the present invention may have, in addition, reinforcing baffles 21 between the outer wall 13 of the microplate and the outer wall 15 of the matrix of wells 9.

The continuous peripheral channel 11 has at least one widening or bulge 22 acting as a filling point for said channel 11. The widening 22 is located in a corner of the microplate 3. The plate 3 has a space 19 on the outside of the base 7 allowing alphanumeric marking of the device.

Example 2

The Examples described here are carried out using 96-well microplates seeded with cell lines at a constant number of cells per well.

The results correspond to measurements of cell viability after 3 or 4 days' incubation in commercially available 96-well microplates compared to identical incubation in microplates whose edges are bordered by aqueous saline solution.

Experiment 1: illustration, in the form of a 3D histogram, of the results of measurement of the cell viability of the line NCI-460 after 72 hours' incubation in an incubator 1. Each of the 96 bars represents a respective value of the signal proportional to the viability corresponding to each well of a standard 96-well microplate in the case of histogram A and, in B, of a microplate according to the invention.

Experiment 2: illustration, in the form of a 3D histogram, of the results of measurement of the cell viability of the line WM 266-4 after 72 hours' incubation in an incubator 2. Each of the 96 bars a represents respective value of the signal proportional to the viability corresponding to each well of a standard 96-well microplate in the case of histogram C and, in D, of a microplate according to the invention.

Experiment 3: illustration, in the form of a 3D histogram, of the results of measurement of the cell viability of the line WM 266-4 after 96 hours' incubation in an incubator 2. Each of the 96 bars represents a respective value of the signal proportional to the viability corresponding to each well of a standard 96-well microplate in the case of histogram E and, in F, of a microplate according to the invention.

The invention claimed is:

1. A microplate comprising a base having a matrix of wells, and an invagination, wherein the depth of the invagination is less than the depth of the wells of the matrix, and wherein the invagination consists of an inner wall and an outer wall which together form a continuous channel around the periphery of the matrix of wells, and at least one bulge, wherein the outer wall of the invagination is juxtaposed to the outer wall of the base and the inner wall is juxtaposed to the outer wall of the matrix at the periphery of the microplate to receive a liquid as an evaporation martyr.

2. The microplate of claim 1, wherein the invagination comprises a liquid which acts as an evaporation martyr, wherein the surface of the liquid in the invagination is nearer to the top of the microplate than a surface of a liquid in the wells of the matrix.

3. The microplate of claim 1, wherein the thickness of the bottom of the invagination is the same as the thickness of the bottom of the wells of the matrix.

4. The microplate of claim 1, wherein the invagination has at least one non-rectilinear wall whose shape matches the wells' circular edges at the periphery of the matrix of wells.

5. The microplate of claim 4, wherein the invagination comprises walls and which are both non-rectilinear, the shape thereof matching the circular edge of the wells at the periphery of the matrix of wells.

6. The microplate of claim 1, wherein the width of the invagination between 2 millimeters and 2.5 millimeters, inclusive, next to the diameter of the wells, and is between 5 to 6 millimeters, inclusive, next to the junction between two wells.

7. A device comprising the microplate of claim 1 and a cover arranged to fully cover the matrix of wells and the invagination of the microplate.

* * * * *